United States Patent
Martin et al.

(10) Patent No.: US 6,730,022 B2
(45) Date of Patent: May 4, 2004

(54) SURGICAL RETRACTOR AND TISSUE STABILIZATION DEVICE HAVING AN ADJUSTABLE SLED MEMBER

(76) Inventors: Thomas E. Martin, 21 Borden St., Riverside, RI (US) 02915; Jennie H. Brown, 10 Rhode Island Ave., Providence, RI (US) 02906; Henry M. Bliss, III, 23 Providence Ave., South Portland, ME (US) 04106; Michael A. Valerio, 44 Ray Rd., Wrentham, MA (US) 02093

( * ) Notice: Subject to any disclaimer, the term of this patent is extended or adjusted under 35 U.S.C. 154(b) by 199 days.

(21) Appl. No.: 10/106,260

(22) Filed: Mar. 26, 2002

(65) Prior Publication Data

US 2002/0099269 A1 Jul. 25, 2002

Related U.S. Application Data

(63) Continuation of application No. 09/489,274, filed on Jan. 21, 2000, now abandoned, which is a continuation-in-part of application No. 09/345,859, filed on Jul. 1, 1999, now Pat. No. 6,348,036.
(60) Provisional application No. 60/117,333, filed on Jan. 24, 1999.

(51) Int. Cl.[7] .................................................. A61B 1/32
(52) U.S. Cl. ...................................................... 600/232
(58) Field of Search ................................. 600/201, 227, 600/228, 231, 232, 233, 235, 234

(56) References Cited

U.S. PATENT DOCUMENTS

| | | |
|---|---|---|
| 3,409,013 A | 11/1968 | Berry |
| 3,509,873 A | 5/1970 | Karlin et al. |
| 3,882,855 A | 5/1975 | Schulte et al. |
| 3,983,863 A | 10/1976 | Janke et al. |
| 4,143,652 A | 3/1979 | Meier et al. |
| 4,151,838 A | 5/1979 | Crew |
| 4,424,724 A | 1/1984 | Bookwalter et al. |
| 4,457,300 A | 7/1984 | Budde |
| 4,461,284 A | 7/1984 | Fackler |
| 4,616,634 A | 10/1986 | Garcia |
| 4,622,955 A | 11/1986 | Fakhrai |
| 4,627,421 A | 12/1986 | Symbas et al. |
| 4,637,377 A | 1/1987 | Loop |
| 4,726,356 A | 2/1988 | Santilli et al. |
| 4,829,985 A | 5/1989 | Couetil |

(List continued on next page.)

FOREIGN PATENT DOCUMENTS

| | | |
|---|---|---|
| CA | 2216893 | 2/1999 |
| DE | 90 04 513.0 | 6/1990 |

(List continued on next page.)

Primary Examiner—Cary E. O'Connor
(74) Attorney, Agent, or Firm—Dechert, LLP; John W. Ryan (57) ABSTRACT

The present invention relates to surgical retractors and devices for stabilizing a predetermined area of the body during a surgical procedure, more particularly to surgical retractors and stabilizing devices used in connection with minimally invasive coronary artery bypass grafting surgical procedures, and more specifically to surgical retractors and stabilizing devices especially configured for use with each other for such surgical procedures wherein the retractor includes a plurality of recessed surfaces thereon for the mounting of a tower type of sled member thereon and wherein the sled member is readily attachable and removable from the retractor and is adjustable upon actuation of an adjustment knob which releasably controls the rotation of the connector with respect to the retractor and the movement of the stabilization arm segment with respect to the retractor upon actuation of a single knob or actuator.

19 Claims, 8 Drawing Sheets

U.S. PATENT DOCUMENTS

| | | |
|---|---|---|
| 4,852,552 A | 8/1989 | Chaux |
| 4,925,443 A | 5/1990 | Heilman et al. |
| 4,949,707 A | 8/1990 | LeVahn et al. |
| 4,973,300 A | 11/1990 | Wright |
| 4,989,587 A | 2/1991 | Farley |
| 5,088,472 A | 2/1992 | Fakhrai |
| 5,098,369 A | 3/1992 | Heilman et al. |
| 5,131,905 A | 7/1992 | Grooters |
| 5,167,223 A | 12/1992 | Koros et al. |
| 5,222,976 A | 6/1993 | Yoon |
| 5,242,240 A | 9/1993 | Gorham |
| 5,337,736 A | 8/1994 | Reddy |
| 5,365,921 A | 11/1994 | Bookwalter et al. |
| 5,383,840 A | 1/1995 | Heilman et al. |
| 5,429,118 A | 7/1995 | Cole et al. |
| 5,452,733 A | 9/1995 | Sterman et al. |
| 5,509,890 A | 4/1996 | Kazama |
| 5,513,827 A | 5/1996 | Michelson |
| 5,514,075 A | 5/1996 | Moll et al. |
| 5,514,089 A | 5/1996 | Walbrink et al. |
| 5,518,503 A | 5/1996 | Rooney et al. |
| 5,529,571 A | 6/1996 | Daniel |
| 5,558,621 A | 9/1996 | Heil |
| 5,613,937 A | 3/1997 | Garrison et al. |
| 5,624,393 A | 4/1997 | Diamond |
| 5,727,569 A | 3/1998 | Benetti et al. |
| 5,730,757 A | 3/1998 | Benetti et al. |
| 5,749,892 A | 5/1998 | Vierra et al. |
| 5,772,583 A | 6/1998 | Wright et al. |
| 5,782,746 A | 7/1998 | Wright |
| 5,836,311 A | 11/1998 | Borst et al. |
| 5,875,782 A | 3/1999 | Ferrari et al. |
| 5,876,332 A | 3/1999 | Looney |
| 5,888,247 A | 3/1999 | Benetti |
| 5,894,843 A | 4/1999 | Benetti et al. |
| 5,947,896 A | 9/1999 | Sherts et al. |
| 5,951,466 A | 9/1999 | Segermark et al. |
| 5,957,835 A | 9/1999 | Anderson et al. |
| 5,967,972 A | 10/1999 | Santilli et al. |
| 5,976,171 A | 11/1999 | Taylor |
| 6,030,340 A | 2/2000 | Maffei et al. |
| 6,036,641 A | 3/2000 | Taylor et al. |
| 6,102,854 A | 8/2000 | Cartier et al. |
| 6,132,370 A | 10/2000 | Furnish et al. |

FOREIGN PATENT DOCUMENTS

| | | |
|---|---|---|
| DE | 297 11 829 | 10/1997 |
| DE | 197 08 587 | 11/1998 |
| EP | 336526 | 10/1989 |
| EP | 356410 | 2/1990 |
| EP | 630629 | 12/1994 |
| EP | 668058 | 8/1995 |
| EP | 791330 | 8/1997 |
| EP | 808606 | 11/1997 |
| FR | 1019217 | 10/1952 |
| GB | 2102681 | 2/1983 |
| GB | 2267827 | 12/1993 |
| WO | WO 87/04081 | 7/1987 |
| WO | WO 94/14383 | 7/1994 |
| WO | WO 95/15715 | 6/1995 |
| WO | WO 95/17127 | 6/1995 |
| WO | WO 97/10753 | 3/1997 |

SURGICAL RETRACTOR AND TISSUE STABILIZATION DEVICE HAVING AN ADJUSTABLE SLED MEMBER

"The present application is a continuation of U.S. Ser. No. 09/489,274 filed on Jan. 21, 2000, now abandoned, which is a continuation-in-part of U.S. Ser. No. 09/345,859 filed on Jul. 1, 1999 now U.S. Pat. No. 6,348,036, Provisional U.S. Ser. No. 60/117,333 filed on Jan. 24, 1999.

FIELD OF INVENTION

The present invention relates to surgical retractors and stabilization devices for engaging a predetermined area of the body during a surgical procedure, more particularly to surgical retractors and stabilizing devices used in connection with coronary artery bypass grafting surgical procedures, and more specifically to surgical retractors and stabilizing devices particularly configured for use with each other for such surgical procedures.

The present application is related to U.S. Ser. No. 60/117,333 filed on Jan. 24, 1999 and U.S. Ser. No. 09/345,859 filed on Jul. 1, 1999 the priority thereof is claimed hereby and the disclosures thereof are incorporated herein by reference.

BACKGROUND OF THE INVENTION

Diseases of the cardiovascular system affect millions of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system leading to the heart.

One technique for treating such a blockage or restriction is a surgical procedure known as a coronary artery bypass graft procedure, which is more commonly known as "a heart bypass" operation. The surgical correction of occluded or stenosed coronary arteries by means of bypass grafting are probably still the most common procedures performed today, especially when multiple grafts are needed.

In the coronary artery bypass graft procedure, the surgeon may remove a portion of a vein from another part of the body for grafting or detaches one end of a local artery and connects that end past the obstruction while leaving the other end attached to the existing arterial supply. When using a vein from another part of the body, the surgeon installs this portion at points that bypass the obstruction. In both cases, the objective is to restore normal blood flow to the heart.

In addition, when using this technique, the surgeon makes a long incision down the middle of the chest, saws through the sternum, spreads the two halves of the sternum apart. In the past, the surgeon then performed several procedures necessary to connect the surgical patient to a cardiopulmonary bypass machine to continue the circulation of oxygenated blood to the rest of the body while the heart is stopped and the graft is being sewn in place. Although such a procedure is one common technique, the procedure is lengthy, traumatic and can damage the heart, the central nervous system and the blood supply of the patient.

Interventional techniques, such as percutaneous transluminal angioplasty (PTCA) have gained popularity as the method of choice for therapy of atherosclerosis occlusions for several reasons. The transluminal approach is a less invasive technique that subjects the patient to fewer traumas and a shorter recovery time, especially when compared to bypass grafts, which utilize homologous tissue, such as saphenous vein grafts. Also, the patient often suffers complications at the donor site of the graft that may be worse than the sternotomy and anastomosis.

Although PTCA procedures are often successful, complications such as restenosis or thrombosis and embolism can occur. Restenosed vessels may often require surgical intervention for correction. The surgical correction of restenosis, like the conventional coronary bypass surgical procedure, oftentimes required the heart to be stopped and the patient placed on a heart/lung bypass machine during the procedure.

In recent years, and in an effort to reduce expense, risk and trauma to the patient, physicians have turned to alternate approaches to heart surgery, including less invasive procedures such as intercostal and endoscopic access to the surgical site. Additionally, beating heart surgery has begun to replace cardiopulmonary bypass surgery using a pump. With such procedures, the heart is beating during the surgical procedure. Thus, there is no need for any form of cardiopulmonary bypass and there is no need to perform the extensive surgical procedures necessary to connect the patient to such a bypass machine.

Over the years, there have been many attempts at performing minimally or less invasive bypass grafting on a beating heart. Until recently, these techniques have been thought of as being dangerous and difficult because of the delicate nature of the surgical procedure, the lack of adequate access through a reduced surgical field, and the lack of a way to adequately stabilize and reduce tissue movement at the graft site. These procedures are performed while the heart muscle is continuing to beat so that the heart continues to move in a three dimensional movement and the blood continues to flow while the surgeon attempts to evaluate the vessel and then sew the graft in place. Also, the surgical procedure to install the graft requires placing a series of sutures through the wall of an extremely small vessel and onto the artery and heart tissue while the heart continuously moves during the procedure. It is necessary that these sutures be fully and securely placed so the graft is firmly in position and does not leak.

There is disclosed in U.S. Pat. No. 5,730,757, an access platform for the dissection of an internal mammary artery. The described access platform has first and second blades interconnected to a spreader member that laterally drives the blades apart together and support pads interconnected to the first blade. A torsional member is operably interconnected to the first blade and the spreader member and is used to vertically displace the first blade in either direction. Thus, increasing the surgeon's working space and visual access for the dissection of the internal mammary artery. A tissue retractor interconnected to the blades is used to draw the soft tissue around the incision away from the surgeon's work area. It is further provided that the access platform can include a port that can be used to mount a heart stabilizer instrument.

There also is described in U.S. Pat. No. 5,875,782 granted to Ferrari et al. and U.S. Pat. No. 5,894,843 granted to Benetti et al. an apparatus for stabilizing the predetermined area on a heart or other organ of a patient to enable a surgical procedure on a beating heart. The apparatus includes a bifurcated member having two elongated prongs and an elongated handle. The handle segment can be movably attached to a rib retractor so that a person is not required to hold the handle segment. In one disclosed embodiment, the apparatus further includes a device to hold the bifurcated member in a desired position against the surface of the heart so that a stabilizing force is applied against the heart.

There also is described in U.S. Pat. No. 5,836,311 granted to Borst et al. an apparatus for stabilizing the predetermined area on a heart or other organ of a patient to enable a surgical procedure on a beating heart. The apparatus includes a single legged or bifurcated member having a plurality of suction members thereon which are attached to the surface of the heart using suction pressure. The arm portion of this device can be movably attached to a rib retractor or other surgical device so a person is not required to hold the handle segment and the suction device may be locked into position against the surface of the heart.

It is therefore desirable to provide a new system and devices related thereto for stabilizing a predetermined area of the body, such as the heart and methods related thereto. It is particularly desirable to provide such a system and devices thereto that are less complex and more user friendly in comparison to prior art devices. Such systems and devices thereto preferably are simple in construction, versatile and are preferably low profile to minimize obstruction of the view of the surgeon or nurse to the surgical field.

SUMMARY OF THE INVENTION

The present invention features a system for retracting, stabilizing or manipulating a predetermined area of a body. The system includes a surgical retractor, a stabilization arm or apparatus and a tissue support or stabilization device, and methods of use related thereto. Also featured is a system that also supports any of a number of surgical implements, for example a diaphragm retractor, a valve retractor, a light or a suction device for use during a surgical procedure. The stabilization system and related devices and apparatuses thereto that are featured herein are particularly advantageous for use in performing off-pump coronary artery bypass grafting procedures in which the heart remains beating during the surgical procedure. One advantage of the present invention relates to the use of the stabilization arm to provide a low profile stabilization system so that obstruction of the physician's view of the surgical site is minimized. Another advantage of the present invention relates to the use of the sled member on the arms of the retractor and even more preferably on the rack segment of the retractor. Additionally, the sled member of the present invention allows for a full range of motion that is controlled by a single knob that is easily manipulated by the surgeon.

The stabilization device preferably includes a device of the type commonly known as the Cohn Cardiac Stabilizer marketed by the Genzyme Corporation of Cambridge Mass., although horseshoe or suction type devices may also be used. The preferred form of the stabilization device is a generally square or rectangularly shaped member having a planar surface with centrally located opening therein. This opening is the area through which the surgeon performs the anastomosis or other procedure on the tissue of the beating heart. The stabilization device is preferably a two piece member so that once the anastomosis is completed, the pieces may be separated to remove the device from around the anastomosis. As described more fully below, flexible tapes are sutured through the tissue and then threaded through the stabilizing device. Once the stabilization device is positioned in the desired orientation and location, the flexible tapes are then pulled snug through the opening of the stabilization device to provide a system which captures the tissue and minimizes the overall movement of the predetermined area of the tissue.

The stabilization arm of the present invention preferably includes an elongated handle having a first or distal end portion and a connector thereon for releasably connecting the stabilization device to the elongated handle first end. This connection allows the stabilization device to be pivotally and slidably moved to a desired position into contact with the predetermined area of the tissue of the patient while minimizing the interference of the stabilization device and stabilization arm with the field of view in the surgical field. The stabilization arm also includes a mounting mechanism or sled member through which the stabilization arm is preferably slidable. The stabilization arm may also be positioned on either side of the vertical pivot point of the sled member to further increase the versatility of the stabilization system to allow the stabilization device to be positioned in the desired location of the surgical site. Alternately, one form of the sled member may also be oriented at an angle relative to the retractor to further increase the versatility of the present invention. Additionally, the stabilization arm may be straight or curved to provide the surgeon with yet another choice to obtain the best access to the desired surgical site.

According to one aspect of the present invention, the arms and rack surface of the retractor are configured with a plurality of mounting surfaces thereon. The mounting surfaces are preferably equally spaced along substantially the entire length thereof. The mounting surface is preferably spaced apart a predetermined and consistent distance from the front edge and is also preferably located on the interconnecting or rack segment of the retractor. Also, the stabilization arm preferably includes a sled member that is configured to removably engage the mounting surface at a desired location on one or more of the arms or the rack segment of the retractor. The sled member includes a lever or knob member for selectively engaging a mounting surface on the arm or rack segment of the retractor so the sled member is removably and adjustably secured to the arms or the rack segment of the retractor.

Each of the features described herein enable the user to determine the optimum position for the stabilization arm and stabilization device while ensuring that the surgeon's view of the surgical site is not unnecessarily obstructed. Additionally, these features allow the present invention to be used in many different medical procedures because of the versatility of system set up and orientation of the components of this invention.

Other aspects and embodiments of the invention are more fully discussed below.

BRIEF DESCRIPTION OF THE DRAWINGS

For a fuller understanding of the nature and desired objects of the present invention, reference is made to the following detailed description taken in conjunction with the accompanying drawing figures wherein like reference numbers denote corresponding parts throughout the several views and wherein:

FIGS. 1 A–C illustrate various perspective views of a stabilization system according to the present invention for stabilizing a predetermined area of a body such as a predetermined area of a heart or other organ of a patient to enable the conduct of a surgical operation or procedure;

FIGS. 3 A–C are various perspective views of a portion of the stabilization system of the present invention illustrating the sled member, stabilization arm and stabilization device of the present invention;

FIGS. 4 A–C are side and elevational views of a further embodiment of the sled member of the present invention;

DESCRIPTION OF THE PREFERRED EMBODIMENTS

Referring now to the various figures of the drawings wherein like reference numbers refer to like elements, there is shown a stabilization system 100 according to the present invention for stabilizing a predetermined area of the body of a human patient such as a predetermined area of a heart or other organ to assist the surgeon in performing the surgical procedure. For the sake of brevity, common components between the various embodiments are described only once and are not necessarily repeated as they relate to each separate embodiment discussed below. The stabilization system of the present invention is particularly useful in connection with single or multiple vessel off-pump coronary artery bypass surgery on a beating heart surgery through a sternotomy or mini-sternotomy.

A surgeon may use the stabilization system 100 to apply a slight contacting or compressive force on the heart in the area where the surgical procedure will be performed so the movement of the local tissue at the surgical site is diminished. In a preferred form of this invention, the stabilization system 100 is used in combination with flexible tapes or sutures or other mechanical means so that the tissue adjacent to the surface of the heart is stabilized or captured using a combination of restraining and stabilizing forces. In certain procedures, it may also be advantageous to place a traction suture around an artery using a needle and suture thread to occlude the blood vessel. These sutures may then be attached to the stabilizing device so that the flow of blood through the blood vessel is selectively restricted.

Systems for stabilizing the heart of a patient are particularly useful for various suturing techniques or procedures. One example of this type of procedure is the performance of an anastomosis for a bypass graft. In this type of procedure, the physician is attempting to suture the circumference of a blood vessel that may be about 1 mm to a moving blood vessel on the surface of the heart. Another area of use of the present invention may be in brain surgery, heart valve surgery or other types of blood vessel surgery where stability is critically important to avoid disastrous consequences or where it is desirable to have a precisely defined surgical field. One skilled in the art will appreciate that the present invention, although advantageously suited for heart surgery, can be used at any location on or within the body where tissue stabilization or isolation of a predetermined area is desired. This includes, but is not limited to, the liver, kidneys, bladder, stomach, intestines, brain and vascular and other soft tissue surgery. Additionally, one skilled in the art will appreciate, as hereinafter described, that the supporting components of the system can be adapted so that any surgical instrument or device can be self-supported during a surgical procedure.

As shown in the drawings, the stabilization system 100 according to the present invention includes a retractor 102, a stabilization sub-system or stabilization arm 104 and a stabilization device 106. The retractor 102 is specifically configured so the stabilization arm 104 can be secured thereto. The retractor 102 preferably includes a rigid L-shaped member 110 having an arm segment 112 and a rack segment 114. The retractor 102 also preferably includes a movable second arm segment 116 having a handle 118 thereon which is movably associated with the L-shaped member 110.

The stabilization arm or sub-system 104 preferably includes an elongate handle or stabilization arm segment 180 and sled member 140 that preferably interconnect the retractor 102 and the stabilization device 106. The stabilization arm segment 180 preferably includes a first end having a distal connector 181 thereon to pivotally and removably retain the stabilization device 106 thereon. The stabilization arm segment 180 is attachable to the retractor 102 by a connector such as a mounting mechanism or sled member 140. The proximal or second end 182 of the stabilization arm segment 180 preferably includes a knob 184 thereon that may be rotatable with respect to the stabilization arm segment 180 to allow the movement of the stabilization device 106 to be pivotal and/or fixed with respect to the stabilization arm segment 180 by manipulating the knob 184 on the proximal end of the stabilization arm segment 180. This arrangement also allows the stabilization device 106 to be mountable on and removable from the distal connector 181.

The preferred form of the stabilization device 106 is generally a rectangular shape having an opening or window area 190 therein. The stabilization device 106 preferably includes a first surface 192 that is generally planar and may include a textured surface thereon to facilitate the engagement between the stabilization device and the tissue of the predetermined area or the heart of the patient. The second surface 194 of the stabilization device 106 preferably includes a post member 196 extending therefrom. The distal connector 181 on the first end of the stabilization arm segment 180 preferably releasably and rotatably engages the post member 196.

As described briefly above, the retractor 102 preferably includes a handle 118 located on the second arm segment 116 and the handle 118 is rotatable for displacing the two arm segments 112, 116 with respect to each other. In the preferred form of this invention, rotation of the handle 118 causes a pair of posts or pinions to sequentially engage the teeth located on the outer edge of the rack segment 114 to increase or decrease the distance between the first and second arms 112 and 116. In a specific illustrative embodiment, the rack segment 114 is configured with a finochetti type of rack as is known to those skilled in the art. In conjunction with the handle 118, the rack segment 114 and movable second arm 116 form a rack and pinion type of means for displacing the arm segments 112, 116 with respect to each other. As shown, this type of rack segment 114 includes a plurality of laterally extending teeth that engage the posts or similar tooth engaging members located in operative contact with the handle 118 of the second arm segment 116. It is anticipated that a variety of mechanisms may be used to move the second arm segment 116 along the rack segment 114. For example, a gear mechanism, a slide and locking mechanism or similar arrangement may be used to accomplish the separation and fixation of the second arm 116 with respect to the first arm 112. It is within the scope of the present invention, however, for the retractor 102 to be configured or designed with any of a number of means known to those skilled in the art for selectively displacing the respective arm segments, 112 and 116 either towards or away from each other in a parallel, obtuse or acute angled manner.

Figure 2:
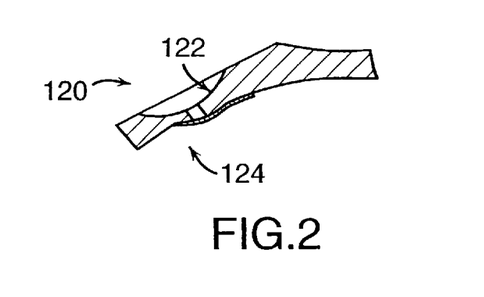
FIG. 2 is a cross-sectional view of the retractor through a mounting surface and having the blade slots removed for clarity.

As indicated above, in a specific illustrative embodiment, the rack segment 114 is configured with a finochetti type of rack as is known to those skilled in the art. The retractor 102 also includes a plurality of blades 128 at least one blade extending outwardly from a surface, the bottom surface, of each arm segment 112, 116. At least one arm segment and preferably both arm segments 112, 116 and/or the rack segment 114 are configured so as to provide at least one mounting point or mounting surface 120 to which a sled member 140 is secured. Preferably, the arm segment and/or the rack segment are configured so as to provide a plurality of such mounting surfaces 120. More particularly, the arm segments, 112 and 116 and/or rack segment 114 are configured with a depressed and generally concave surface 122 in the top surface of the arm/rack segment and a corresponding arcuate or convex surface 124 on the bottom surface thereof to form each mounting surface 120 as shown in FIG. 2. Although convex and concave surfaces are illustrated, it is within the scope of the present invention for these surfaces to have nearly any shape, including a generally arcuate shape. For example, the convex surface on the backside of the art could be a concave or other surface.

Slots 126 are preferably formed in a portion of each mounting surface 120. Preferably, the slots 126 form a generally X-shaped pattern in the concave surface 122 with a through hole centered in the bottom of the depressed surface. However, other slot patterns such as an Y-shaped pattern or a star shaped pattern are within the scope of the present invention. Preferably, a portion of the slots also is arranged so as to extend through the front edge 119 of the arm/rack segment so a portion of the shaft 142 of the sled member 140 can pass therethrough to the centrally located through hole.

Figure 1A:
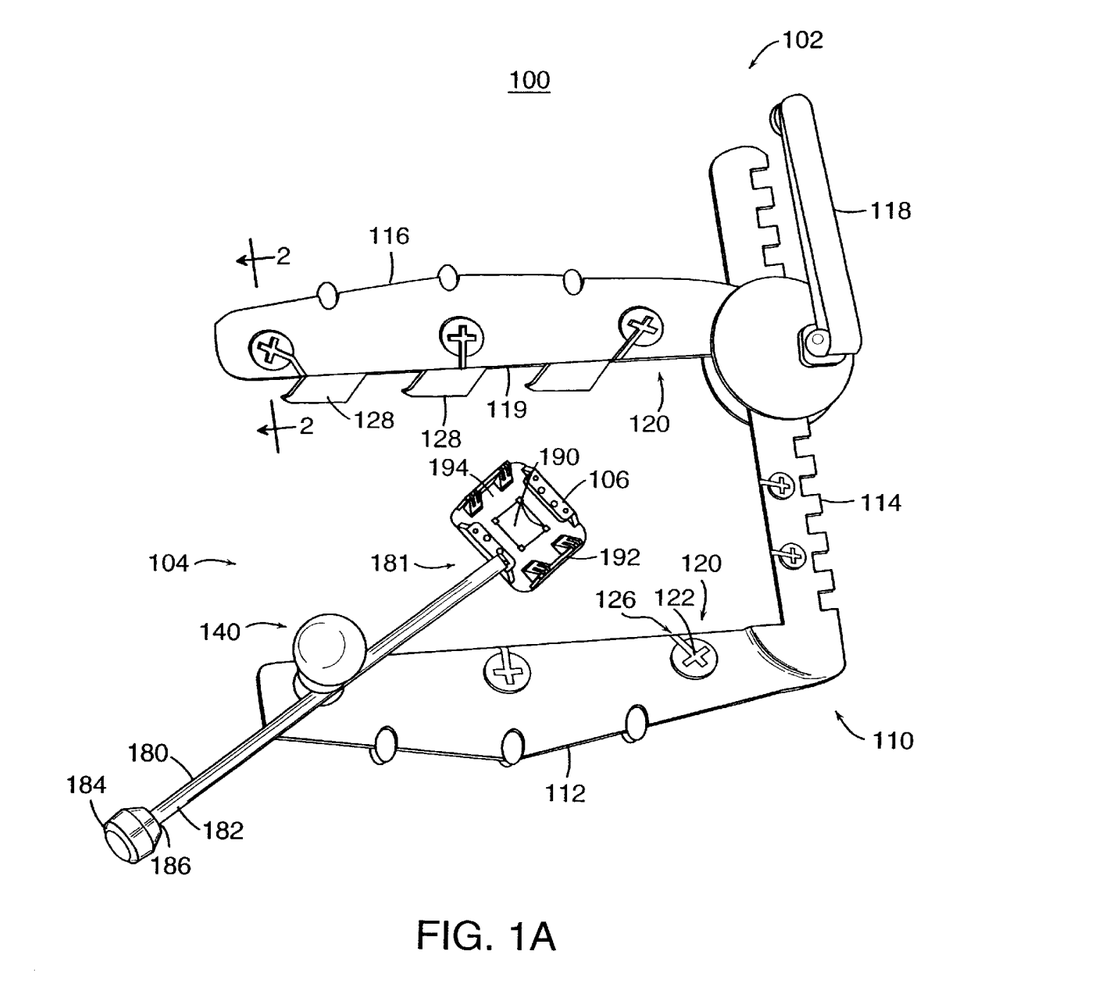
Figure 1B:
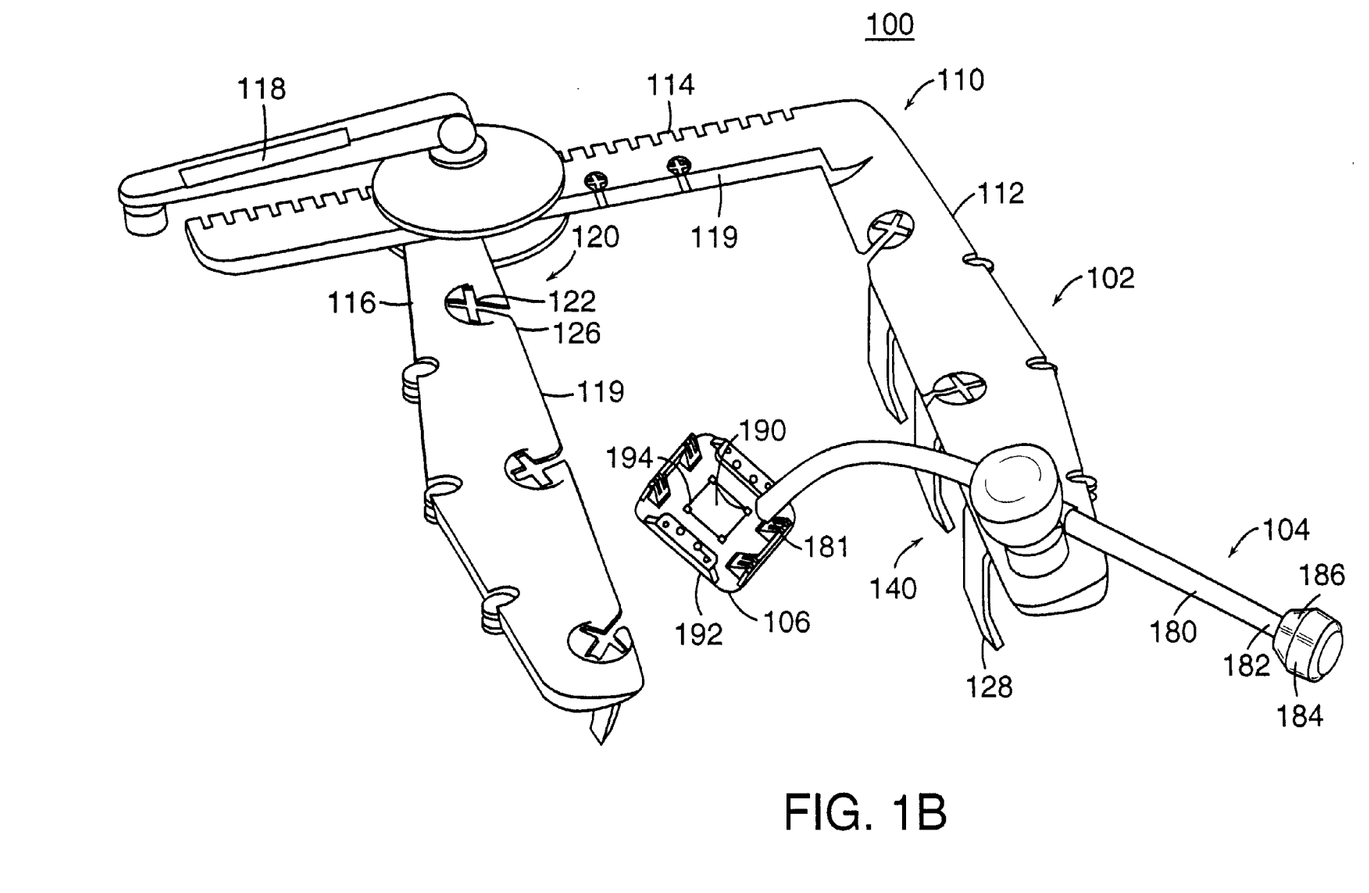
Figure 1C:
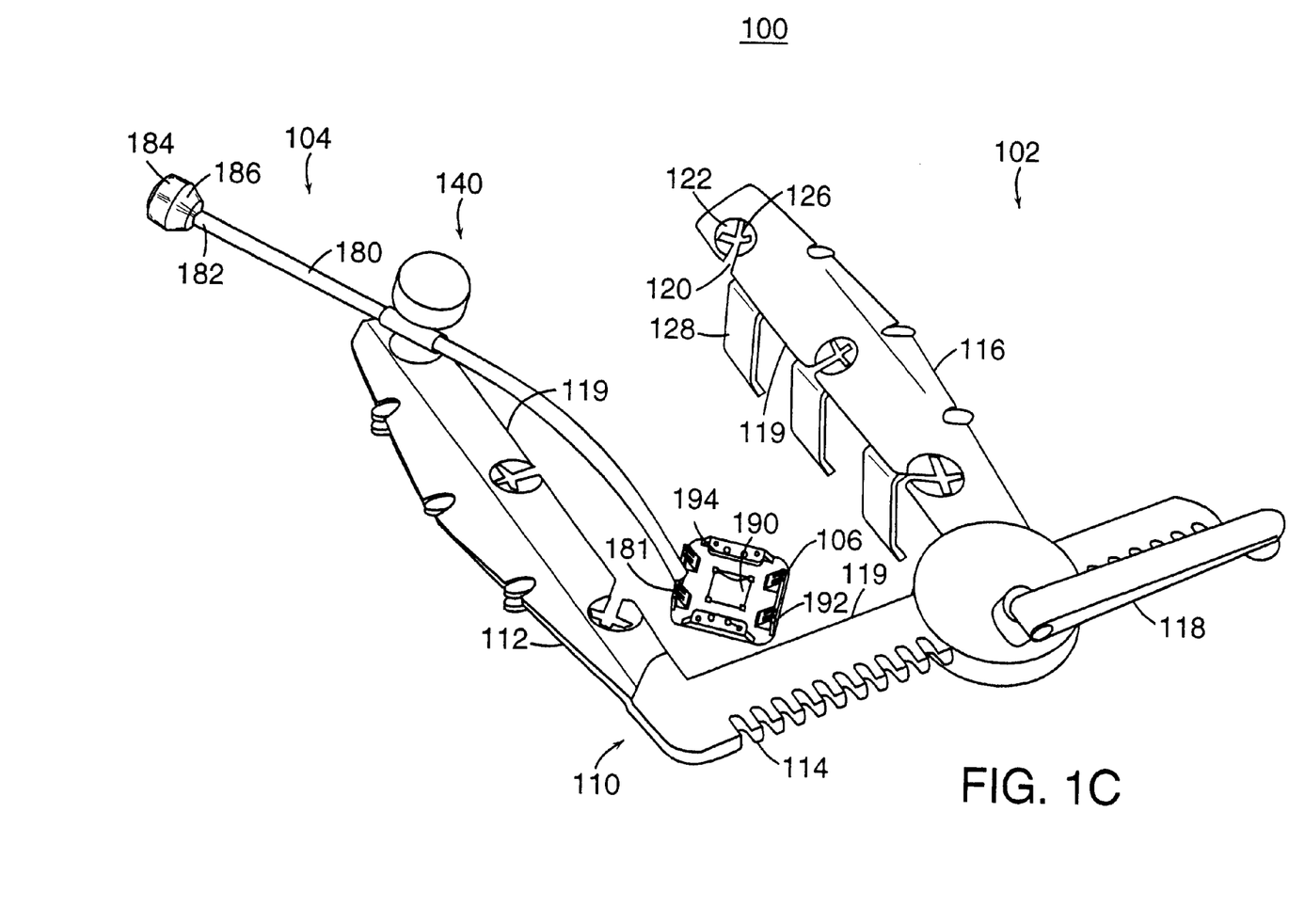

As shown in FIGS. 1A–C, the stabilization arm segment 104 includes the stabilization arm segment 180 and the sled member 140. The sled member 140 is configured so the surgeon can position the stabilization arm segment 180 along the retractor 102 to stabilize the predetermined area of the patient. The sled member 140 is also configured so the surgeon, after positioning the stabilization device 106, can secure the stabilization device 106 and the stabilization arm segment 180 to the retractor 102 so the stabilization device 106 remains fixed in this position without further input or action by the surgeon.

Figure 3A:
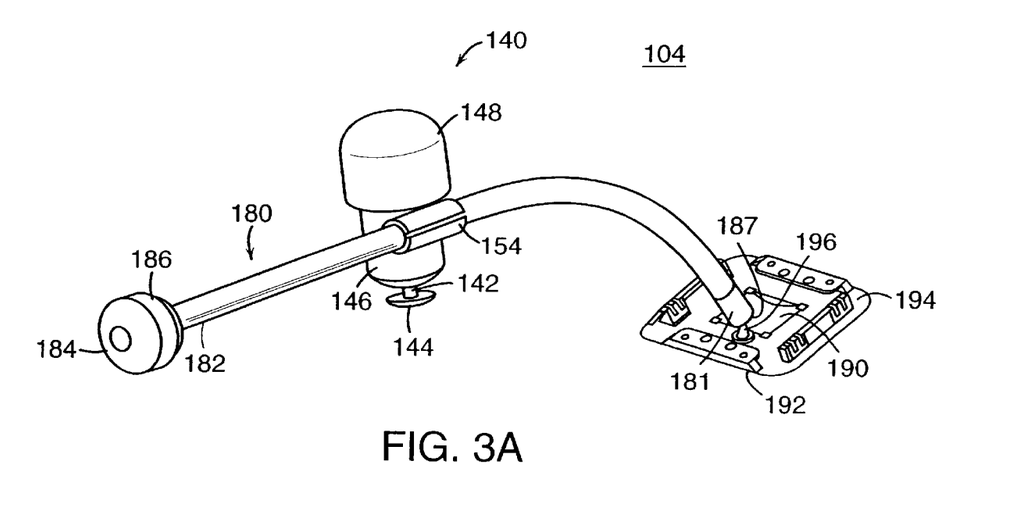
Figure 3B:
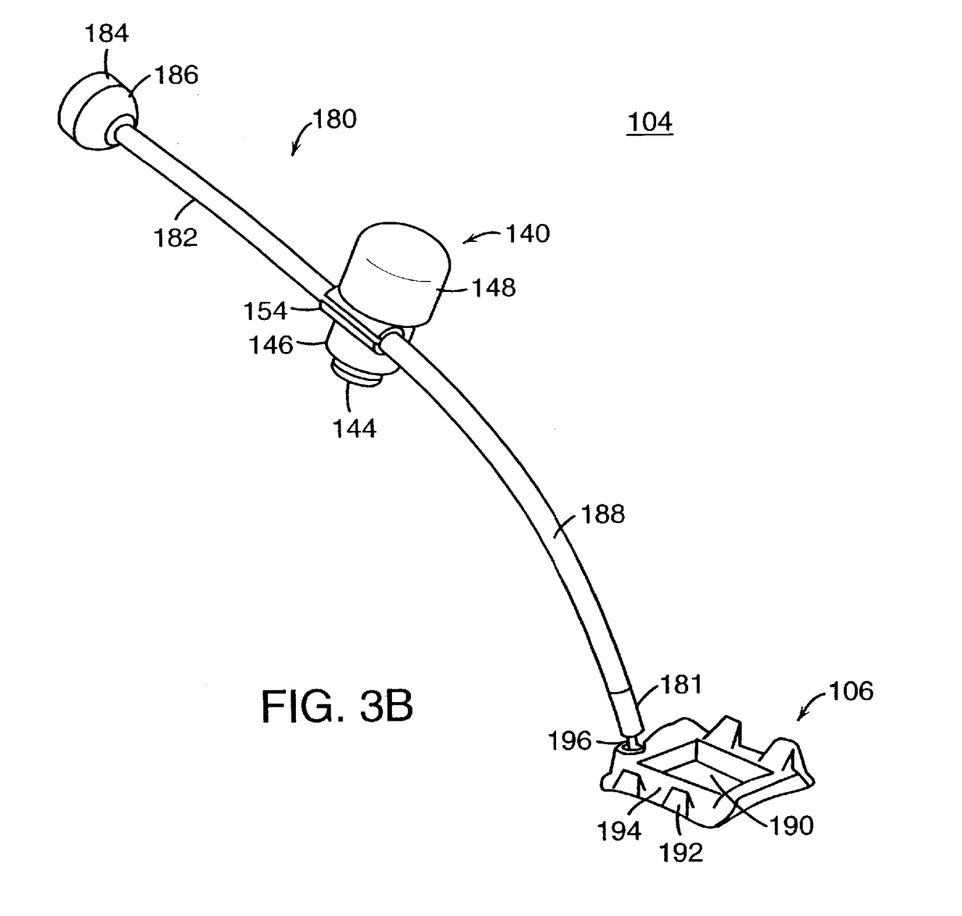
Figure 3C:
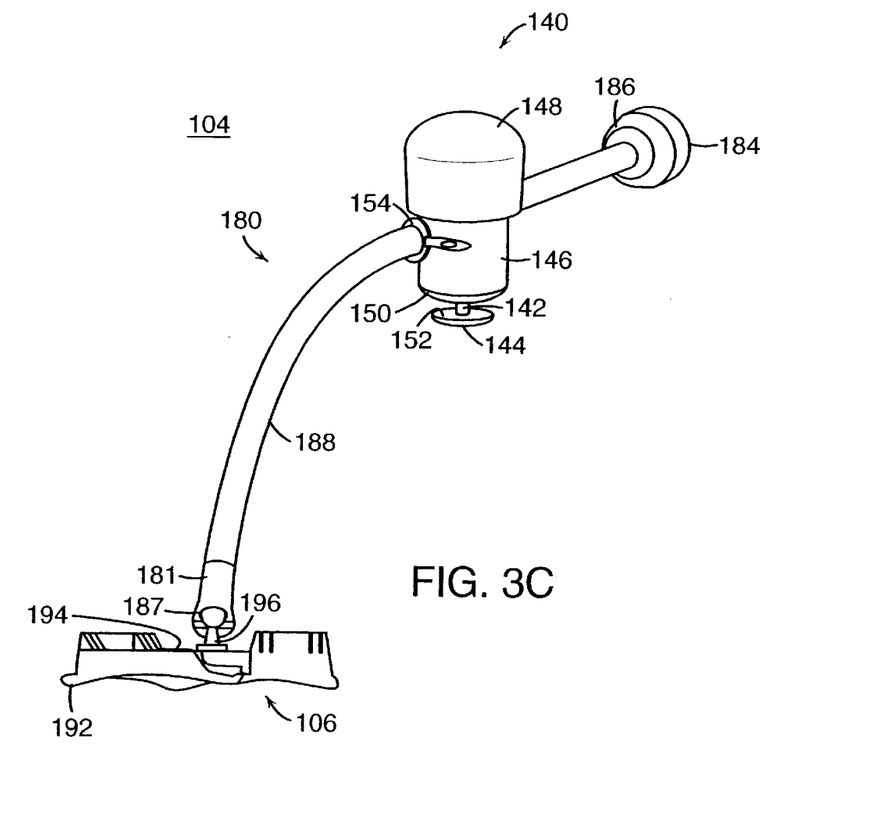

Referring also to FIGS. 3A–C, the sled member 140 includes a washer member 144, a shaft 142, a clamp mount housing 146, and an adjustment knob 148. The lower surface 150 of the clamp mount housing 146 is configured and arranged so as to complement the shape or configuration of the concave surface 122 of each mounting surface 120. This is done so the surgeon can translate or rotate the sled member 140 while the lower surface 150 is disposed within the depression of the mounting surface 120. The upper surface 152 of the washer member 144 also is configured and arranged so as to complement the shape or configuration the convex surface 124 forming each mounting surface 120.

The shaft 142 is rotatably mounted within the adjustment knob 148 and a distal end thereof is rotatably secured to the washer member 144 so rotation of the knob in one direction causes the washer member to be drawn to the lower surface 150 of the clamp mount housing 146. Correspondingly, if the knob is rotated in the opposite direction, the washer member 144 is urged away from the lower surface 150 of the clamp mount housing 146. The shaft 142 is also rotatably disposed within the clamp mount housing 146 so it generally extends along a long axis of the clamp mount housing.

When the sled member 140 is disposed at a mounting surface 120 and the adjustment knob 148 is rotated so the washer member 144 is drawn towards the lower surface 150 of the clamp mount housing 146, the upper surface 152 of the washer member 144 comes into contact with and engages the convex surface 124 on the backside of the retractor arm/rack. Correspondingly, the lower surface 150 of the clamp mount housing 146 is drawn towards the concave surface 122 of the mounting surface 120 with such a rotation of the adjustment knob 148. When the housing lower surface 150 and the washer member upper surface 152 are in contact with and engage the concave and convex, 122 and 124, respectively, the continued rotation of the adjustment knob 148 compresses the clamp mount 154 so as to secure the stabilization arm segment 180 to the clamp mount housing 146.

Accordingly, the inner diameter of the clamp mount 154 is established so the stabilization arm segment 180 is secured therein when the adjustment knob 148 is turned a specified number of revolutions. The inner diameter is also established such that for a lesser number of revolutions, the stabilization arm segment 180 remains slidably disposed within the clamp mount 154 so the surgeon can appropriately position the stabilization device 106 in the surgical site.

The stabilization arm segment or sub-system 104 preferably includes a curved and elongate stabilization arm segment 180 that is preferably formed of a tubular member 188. The stabilization arm segment 180 preferably includes a first end having a distal connector 181 thereon to pivotally and removably retain the stabilization device 106 thereon. The stabilization arm segment 180 is attachable to the retractor 102 by a connector such as the mounting mechanism or sled member 140. The proximal end of the stabilization arm segment 180 preferably includes a movable knob 184 thereon that is rotatable with respect to the stabilization arm segment 180 to allow the movement of the stabilization device 106. The movable knob 184 allows the stabilization device 106 to be fixed, removable and/or pivotal with respect to the stabilization arm segment 180 by manipulating the movable knob 184 on the proximal end of the stabilization arm segment 180. This arrangement also allows the stabilization device 106 to be mountable on and removable from the distal connector 181 such that the stabilization device 106 may be disposable while the stabilization arm segment may be reusable.

A fixed knob 186 is fixed distally of the movable knob 184 on the tubular member 188 of this embodiment to allow the user to rotate the stabilization device 106 and stabilization arm segment 180 by manipulating the fixed knob 186. The movable knob 184 is preferably threadable into the proximal end of the fixed knob 186. Clockwise movement of the movable knob causes an elongate rod member to move distally within the stabilization arm segment 180 to press a pin member in the distal connector 181 against the post member 196 of the stabilization device 106 in a slot 187 in the distal connector 181. Counterclockwise movement of the movable knob allows the elongate rod member to move proximally within the stabilization arm segment 180 to release the pin member and allow the post member to pivot or be removed from the slot 187.

The stabilization device 106 of the stabilization system 100 may be any number of devices that are available for use to contact and engage a predetermined area of the body as well as providing a window or access through which is presented the area targeted by the surgical or, medical procedure to be performed. Such devices include, but are not limited to a Cohn Cardiac stabilizer supplied by Genzyme Surgical Products of Fall River Mass., USA or a bifurcated design provided by numerous companies.

Figure 4A:
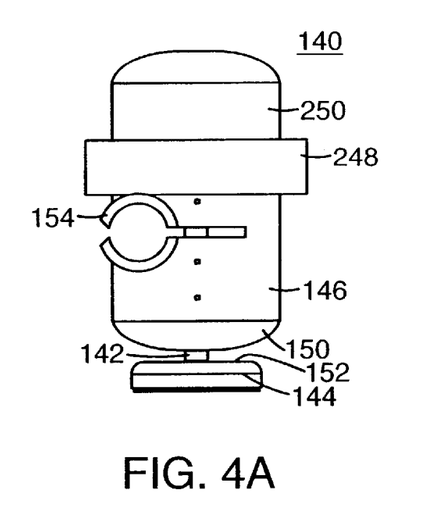
Figure 4B:
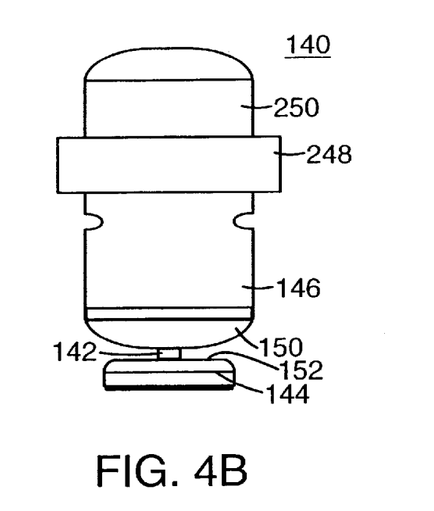
Figure 4C:
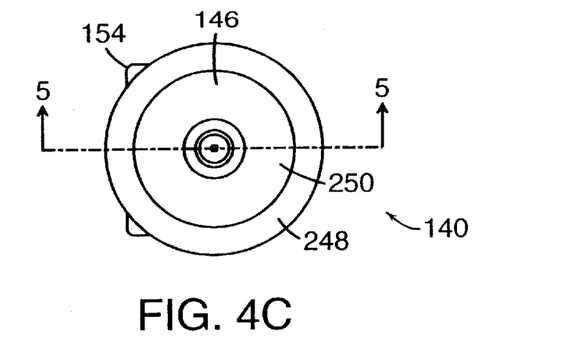
Figure 5:
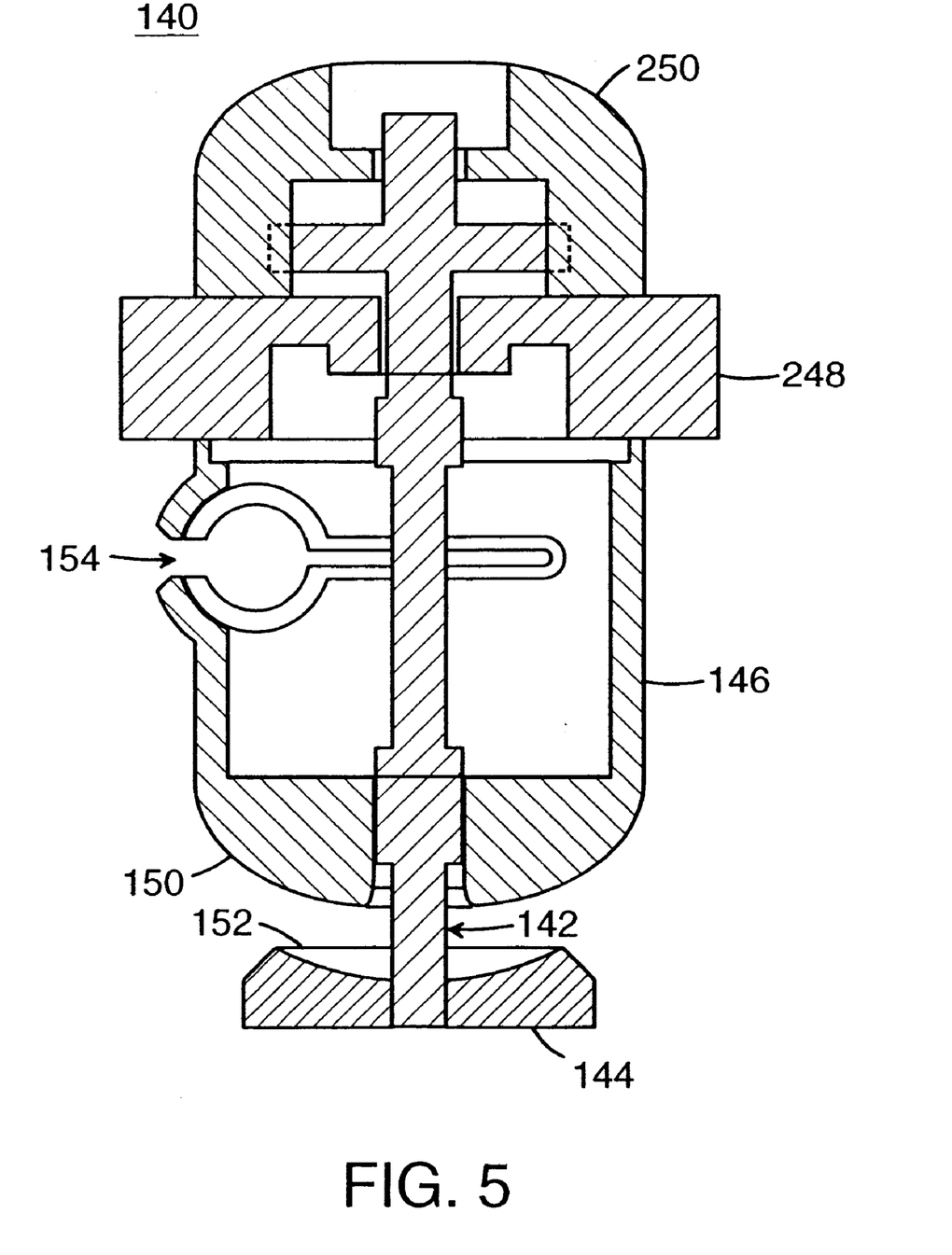
FIG. 5 is a cross sectional view of the sled member shown in FIGS. 4 A–C taken generally along lines 5—5 of FIG. 4A.

There are shown in FIGS. 4 A–D various views of an alternative embodiment for a sled member 140 for use in the stabilization system 100 according to a further form of the present invention wherein like numbers are used for like elements. The sled member 140 includes a washer member 144, a shaft 142, and a clamp mount housing 146, a first adjustment knob 248 and a second adjustment knob 250. The washer member 144 preferably includes an upper surface 152 thereon. The upper surface preferably has a shape that is complementary to the bottom surface of the mounting surface on the retractor. The clamp mount housing 146 preferably includes a lower surface 150 shaped to generally conform to the upper surface of the mounting surface on the retractor. As shown, the clamp mount housing 146 also preferably includes the clamp mount 154 therein. The clamp mount 154 is sized to receive the stabilization arm segment 180 therein and is compressible to engage the stabilization arm segment therein as the knobs 248 and 250 are rotated. Reference should be made to the foregoing discussion for the related components.

In the embodiment, shown in FIGS. 4A–C and 5, the first and second adjustment knobs 248 and 250 act separately on the shaft 142. The first adjustment knob 248 is configured to draw the shaft upwardly when it is rotated in one direction so as to draw the washer member 144 towards the housing lower surface 150. The first adjustment knob 248 is configured, however, so the washer member upper surface 152 and the housing lower surface 150 cannot be placed in firm engagement with the concave and convex surfaces 122, 124 at the mounting surface when the first adjustment knob 248 has been rotated its maximum extent. Rather, the maximum extent of rotation for the first adjustment knob 248 is set so the sled member 140 cannot be withdrawn from the mounting surface but can be translated within the depressed region at the mounting surface 120 by the surgeon for purposes of positioning the stabilization device 106.

The second adjustment knob 250 of this embodiment is configured so it draws the shaft 142 of the sled member 140 upwardly when it is rotated in one direction so the housing lower surface 150 and the washer member 144 of the sled member 140 engage the concave and convex surfaces 122, 124 of the mounting surface 120 thereby securing the sled member to the retractor arm or rack segment 112, 114. Such rotation also causes the clamp mount 154 to be compressed thereby clamping the stabilization arm segment 180 therein. In this way, the stabilization device 106 can remain in contact with and engage the predetermined area without further action or input by the surgeon (i.e., self-supporting).

Figure 6:
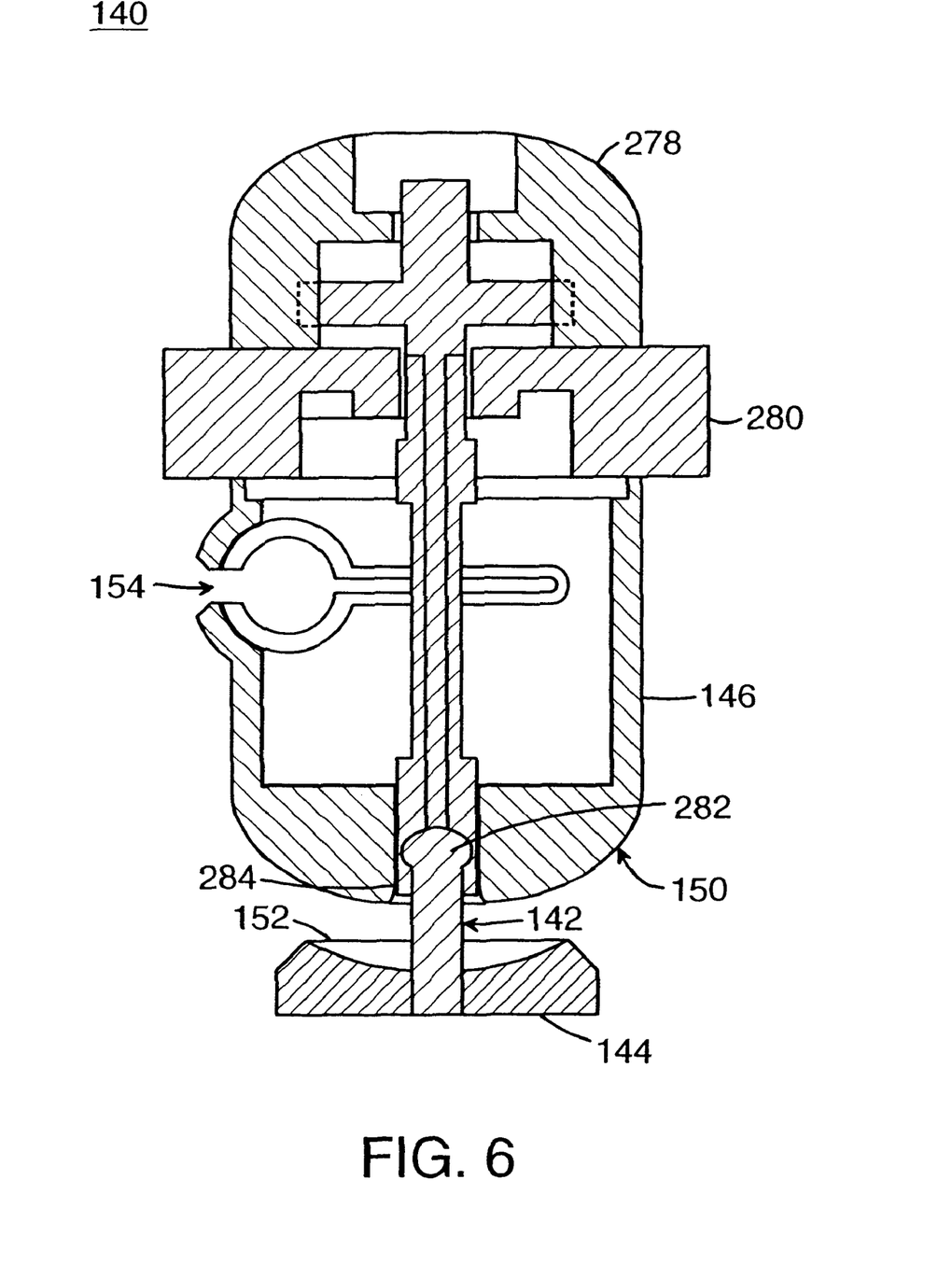
FIG. 6 is a cross sectional view of a further embodiment of a sled member of the present invention taken generally along the same lines as lines 5—5 of FIG. 4A.

In an alternate embodiment, as shown in FIG. 6, the first and second adjustment knobs 278 and 280 act separately on the shaft 142 and washer member 144. For the sake of brevity, like numbers are used to designate like elements referred above. The first adjustment knob 278 is configured to apply pressure against a ball member 282, which extends upwardly from the washer member 144. The ball member 282 is captured in a housing 284 and enables the user to adjust the orientation of the clamp mount housing 146 relative to the washer member 144 such that the clamp mount housing 146 and the stabilization arm segment 180 may be tilted or oriented at an angle relative to the washer member 144 and therefore at an angle relative to the retractor 102. The second adjustment knob 280 is configured to draw the shaft upwardly when it is rotated in one direction so as to draw the washer member 144 towards the housing lower surface 150 and also apply a compressive force against the stabilization arm segment 180 to securely retain the stabilization arm segment in the desired position. The first adjustment knob 278 is configured so the washer member upper surface 252 and the housing lower surface 150 may be oriented at various angles relative to each other prior to the placement of the clamp mounting housing 146 in firm engagement with the concave and convex surfaces 122, 124 of the mounting surface 120. Rather, the rotation for the first adjustment knob 278 is set so the shaft engages the ball member 282 to prevent further rotation of the washer member 144 relative to the clamp mount housing 146 when the first adjustment knob 278 is tightened.

The second adjustment knob 280 of this embodiment is configured so it draws the shaft 142 of the sled member 140 upwardly when it is rotated in one direction so the housing lower surface 150 and the washer member 144 securely engage the concave and convex surfaces 122, 124 of the mounting surface 120 thereby securing the sled member 140 to the retractor arm or rack segment. Such rotation also causes the clamp mount 154 to be compressed thereby clamping the stabilization arm segment 180 therein. In this way, the stabilization device 106 can remain in contact with and engage the predetermined area without further action or input by the surgeon (i.e., self-supporting).

The stabilizing systems according to the further embodiments of the present invention are used in a similar manner as the stabilizing system 100 of the first aspect of the invention. The principle difference being the manner in which the stabilization arm segment 104 is mounted to the retractor 102 and the manner in which the surgeon would adjust the stabilization device 106 such that it is contact with and engaging the predetermined area. As such the following describes the mounting of the sled member and adjustment of the stabilization device 106, with reference to each of the Figures.

After the surgeon has retracted the tissue and the sternum, by outwardly disposing the retractor arm segments 112, 116, the surgeon mounts the stabilization arm segment 104 to one of the mounting surfaces 120 on an arm segment 112, 116 or rack segment 114. To accomplish this the surgeon first slides the portion of the shaft located between the housing lower surface and the washer member upper surface through the portion of the slot 126 that extends to the front edge of the retractor arm, 112 or 116, or rack segment 114 for a mounting surface 120. This is done until the housing lower surface is generally opposite to the concave surface 122 of the mounting surface 120. In one of the embodiments described above, the surgeon may adjust the relative orientation of the clamp mount housing and the washer member to adjust the angle of approach by the stabilization arm segment to the surgical site.

The surgeon may then rotates the adjustment knob or knobs a number of turns to reduce the spacing between the housing lower surface and the washer member upper surface so the sled member cannot slide back out the slot 126. For one or more embodiments of the alternate embodiments of the sled member described above, the surgeon may rotate the first adjustment knob to its maximum extent so as to accomplish the same effect.

To securely and finally position the stabilizer device 106, the surgeon then may do any one or more of the following (1) translate the sled member within the depressed region of the mounting surface 120, including using the other slots formed in the concave surface 122, (2) rotate the sled member about the shaft, (3) slide the stabilization arm segment 180 within the clamp mount of the clamp mount housing, (4) pivot the stabilization device 106 about the distal connector 181 of the stabilization arm segment 180 or (5) adjust the angle of the clamp mount housing relative to the retractor. After the stabilization device 106 has been positioned at the desired area, the surgeon rotates the movable knob 184 on the stabilization arm segment so as to prevent further movement of the stabilization device 106 with respect to the distal connector 181 of the stabilization arm segment 180. The surgeon also rotates the appropriate adjustment knob of the sled member so the housing lower surface and the washer member upper surface firmly engage the concave and convex surfaces 122, 124 of the mounting surface 120 thereby securing the sled member at the desired mounting surface 120. Additionally, such rotation also compresses the clamp mount to securely clamp the stabilization arm segment 180 therein. For the alternative embodiments of the sled members, the surgeon rotates the first and/or second adjustment knobs so as to accomplish the same securing and clamping effect.

As indicated above, it is within the scope of the present invention for the stabilization device 106 to be replaced with any of a number of stabilization devices known to those skilled in the art, for example a Cohn Cardiac Stabilizer manufactured by Genzyme Surgical Products Corporation of Cambridge, Mass., U.S.A. Additionally, although the stabilization arm segment 180 is illustrated as being a curved member, the stabilization arm segment can include an arcuate section, be sinuous or straight.

In the foregoing discussion, the sled member of any of the embodiments of the invention is described in terms of clamping and supporting a stabilizer. It is within the scope of the present invention, however, for the support to be configured to removably secure any of a number of surgical instrumentalities to the retractor such as for example valve or diaphragm retractors. Additionally, although one support is described as being in use at a time, it is within the scope of the present invention for plurality or a multiplicity of supports to be secured to the retractor. For example, one sled member could be provided to support a diaphragm retractor and another sled member to support a stabilizer.

Although various preferred embodiments of the present invention have been described using specific terms, such description is for illustrative purposes only, and it is to be understood that changes and variations may be made without departing from the spirit or scope of the following claims.

What is claimed is:

1. A system for self-supporting a surgical instrument, comprising: a retractor;
 a surgical instrument support for securing the surgical instrument to the retractor; wherein the retractor includes:
  (a) a pair of arms having a lengthwise dimension, inner and outer surfaces and top and bottom surfaces and an interconnecting member for selectively orienting the arms and the interconnecting member in a desired relationship with the body of a patient with the inner surfaces of the arms facing each other, and
  (b) wherein at least one of the arms include a plurality of slots extending inwardly from the inner surface of the arm and further having a plurality of mounting surfaces in communication with the slots and extending through the top and bottom surfaces of the arm and wherein the mounting surfaces and slots are configured to removably receive one end of the surgical instrument support thereon; and
 wherein the surgical instrument support includes:
  a sled member for securing the surgical instrument support to one of the one or more arms and the interconnecting member,
  a clamping member for selectively securing at least a portion of the surgical instrument support to the surgical instrument, whereby the clamping member is sized to be slidable through one of the slots and into operative contact with the mounting surface such that the surgical instrument is supportable by the retractor during a procedure; and
  wherein an actuation member on the sled member is pivotal with respect to the arms of the retractor when said clamping member is in operative contact with said mounting surface and actuation of the actuation member in a first direction causes the clamping member of said sled member to engage the selected arm of the retractor and also causes the clamping member to secure the surgical instrument support to a portion of the surgical instrument.

2. The system for self-supporting a surgical instrument of claim 1, wherein the interconnecting member further includes an interconnecting segment having an inner and outer surface and wherein the inner surface includes a slot thereon that extends inwardly to a mounting surface thereon and wherein the mounting surface extends through the top and bottom surfaces on the interconnecting segment and the mounting surface is configured to removably receive the clamping member of the surgical instrument support therethrough to secure the surgical instrument support to the retractor.

3. The system for self-supporting a surgical instrument of claim 1, wherein both arms of the retractor include slots and mounting surfaces extending inwardly from the inner surfaces thereof and wherein the mounting surfaces are configured to removably receive the sled member of the surgical instrument support therethrough to fixedly retain the sled member of the surgical instrument support to an arm of the retractor by positioning the sled member adjacent to the mounting surfaces and extending through the top and bottom surfaces of the selected arm of the retractor.

4. A system for stabilizing a predetermined area of a patient, comprising:
 a retractor;
 a stabilization assembly for contacting the predetermined area of a patient wherein the stabilization assembly includes;
  (a) a stabilization arm segment having an elongated handle having a first end and a sled member that secures the stabilization arm segment relative to the retractor, wherein the retractor has top and bottom surfaces and includes:
   (a) a plurality of arms,
   (b) an interconnecting member for selectively spacing the plurality of arms apart from each other and for maintaining the plurality of arms in a desired spaced apart relationship, and
   (c) wherein the arms and interconnecting member include inner and outer surfaces wherein said inner surfaces are oriented to face each other and at least one of the plurality of arms includes a slot extending inwardly from the inner surface thereof and a mounting surface in communication with said slot and wherein the mounting surface extends through the arm and is configured to removably receive the sled member thereon; and
  wherein the sled member includes:
   (a) a clamping member on the sled member for extending through and removably securing the sled member to the mounting surface of the at least one retractor arm, and (b) a handle engaging member on the sled member for selectively securing the sled member to a portion of the elongated handle, (c) an actuation member on the sled member operatively associated with the clamping member and the handle engaging member wherein operation of the actuation member to a first position causes the clamping member to secure the sled member to the mounting surface on the retractor and causes the sled member to engage a portion of the elongate handle to thereby interconnect the stabilization device to the retractor and operation of the actuation member to a second position allows the handle member and retractor to be movable relative to the sled member wherein the sled member engages the top and bottom surfaces of the arm of the retractor in the first position and is spaced apart therefrom in the second position thereof.

5. The system for stabilizing a predetermined area of a patient of claim 4, wherein the sled member includes a longitudinal axis and the longitudinal axis is oriented to extend through the mounting surface and intersect the top and bottom surfaces of the retractor and the actuation member is movable along the longitudinal axis of the sled member between the first and second positions thereof.

6. The system for stabilizing a predetermined area of a patient of claim 4, wherein the plurality of arms of the retractor include slots and mounting surfaces thereon that are configured to removably receive the sled member therethrough and wherein the sled member is pivotal relative to the arm of the retractor in at least the second position of the actuation member when the sled member is received through the mounting surface.

7. The system for stabilizing a predetermined area of a patient of claim 4, wherein the plurality of arms of the retractor are configured with a front edge and a recessed area in at least one of the plurality of arms and wherein the recessed area is spaced from the front edge of the arms and extends therethrough to form the mounting surface; and wherein the clamping member of the sled member includes a pair of members that are movable relative to each other and an actuation member which extends therealong and causes the pair of members to selectively engage the top and bottom surfaces of the retractor adjacent to the recessed area so the sled member is secured to at least one of the plurality of arms in the first position of the actuation member.

8. The system for stabilizing a predetermined area of a patient of claim 4, wherein each of the plurality of arms and at least a portion of the interconnecting member is configured with a front edge and a slot in communication with a recessed area on a surface of the mounting surface and the recessed area is spaced apart from the front edge; and wherein the clamping member includes a shaft member that extends through the mounting surface and a pair of members that are movable relative to each other and at least one of the pair of members includes a surface thereon for engaging a surface of the recessed area so the sled member is removably secured to one of the interconnecting member and the plurality of arms when the shaft member is received through the slot on the retractor.

9. A system for use in a surgical procedure, comprising:
a retractor having top and bottom surfaces and a plurality of retractor arms thereon and a segment interconnecting the retractor arms wherein said retractor arms include a front edge surface, a plurality of recessed areas extending through the retractor arms and interconnecting segment and a plurality of slots extending from the front edge surface to the recessed areas and wherein the arms are movable with respect to each other;

a stabilization assembly including a sled member and an elongate handle member having distal and proximal end portions and the sled member includes a shaft extending therethrough and the shaft extends through a recessed area so the stabilization assembly is operatively positionable with respect to the retractor and the sled member is retained on the retractor when the shaft member extends through the recessed area and the sled member further includes a clamp mount with a clamping member that is sized to hold the handle member in a desired position during a medical procedure; and a connector which is removably attached to the distal end portion of the handle member and wherein the sled member extends through the slot and recessed area on the retractor and engages an arcuate surface on one of the top and bottom surface of the retractor adjacent to the recessed area.

10. The system of claim 9 wherein the sled member includes an actuation member and a clamping member thereon and wherein the clamping member includes a pair of movable members thereon and which engage the top and bottom surface of the retractor adjacent to the recessed areas in response to actuation of the actuation member on the sled member and wherein the clamping member is rotatable relative to the arcuate surface on the retractor.

11. The system of claim 10 wherein the sled member includes a longitudinal axis extending between the clamping member and the actuation member and at least a portion of the retractor forms a horizontally oriented surface and the longitudinal axis of the sled member is pivotal relative to the horizontally oriented surface of the retractor as the clamping member is rotated relative to the arcuate surface.

12. The system of claim 11 wherein rotational movement of the actuation member causes the clamping member to compress and engage the top and bottom surfaces of the retractor and further causes the sled member to engage the handle segment in the same rotational position of the actuation member.

13. The system of claim 11 wherein the longitudinal axis of the sled member includes a pivotal member therealong to enable the sled member to pivot relative to the horizontally oriented surface of the retractor.

14. The system of claim 11 wherein rotation of the actuation member on the end portion of the sled member enables the longitudinal movement of the handle member of said stabilization assembly to directly enable the slidable movement of the connector on the distal end portion of the handle member relative to the retractor.

15. The system of claim 11 wherein the sled member further includes a mounting member for engaging the handle member and the mounting member is offset from the vertical axis of the sled member.

16. The system of claim 9 wherein the clamping member of the sled member includes top and bottom surfaces thereon that are complementary to the top and bottom surfaces of the retractor and the clamping member is insertable through the slot and the top and bottom surfaces of the clamping member are positionable adjacent to the recessed area on the retractor.

17. The system of claim 16 wherein the clamping member engages a pair of oppositely oriented recessed areas on the retractor to fixedly position the sled member on the retractor and the sled member is pivotal with respect to the retractor.

18. The system of claim 17 wherein the recessed areas on the retractor are spaced apart from the front edge surface of the retractor and the clamping member is receivable through the slot on the retractor.

19. A method for stabilizing the heart of a patient with a device having a stabilization arm segment and a stabilization device operatively connected to a retractor platform, the method steps comprising: providing a retractor platform having a top surface and a bottom surface, at least a portion of the bottom surface configured for contacting the skin surface of the patient and the retractor platform including a front edge surface with a slot therein and wherein the slot is in communication with a recessed surface that extends through the platform, positioning a sled member on the retractor platform by sliding a shaft portion of the sled member through the slot and into the recessed surface of the retractor platform, rotating an actuation member on the sled member to cause a portion of the sled member to clamp the portion of the top and bottom surfaces of the retractor platform therebetween adjacent to the recessed surface, and engaging a handle member having a connector thereon with the sled member upon rotation of the actuation member to cause the stabilization device to contact a surface of the heart of a patient wherein the handle member and sled member are movable with respect to the retractor platform in a first position of the actuation member and the handle member and sled member are fixedly positioned with respect to the retractor in the second position of the actuation member.

* * * * *